(12) United States Patent
Clavelle et al.

(10) Patent No.: US 11,426,091 B2
(45) Date of Patent: Aug. 30, 2022

(54) FILM COATINGS AS ELECTRICALLY CONDUCTIVE PATHWAYS

(71) Applicant: Apple Inc., Cupertino, CA (US)

(72) Inventors: Adam T. Clavelle, San Francisco, CA (US); Martin Melcher, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 595 days.

(21) Appl. No.: 16/128,210

(22) Filed: Sep. 11, 2018

(65) Prior Publication Data

US 2019/0069848 A1    Mar. 7, 2019

Related U.S. Application Data

(63) Continuation-in-part of application No. 16/122,811, filed on Sep. 5, 2018, now abandoned, and a
(Continued)

(51) Int. Cl.
*A61B 5/00* (2006.01)
*A61B 5/024* (2006.01)
(Continued)

(52) U.S. Cl.
CPC ...... *A61B 5/02438* (2013.01); *A61B 5/02427* (2013.01); *A61B 5/6824* (2013.01);
(Continued)

(58) Field of Classification Search
CPC .............. A61B 5/6824; A61B 5/02427; A61B 5/02438; H05K 5/0095
See application file for complete search history.

(56) References Cited

U.S. PATENT DOCUMENTS 3,646,562 A    2/1972 Acker et al.
4,059,956 A *  11/1977 Maeda ................ G04G 21/08
                                                 368/224
(Continued)

FOREIGN PATENT DOCUMENTS

JP    2002165768 A  *  6/2002
JP    2007075174 A  *  3/2007
(Continued)

OTHER PUBLICATIONS

U.S. Appl. No. 16/122,811, "First Action Interview Pilot Program Pre-Interview Communication", dated Oct. 1, 2019, 14 pages.
(Continued)

*Primary Examiner* — Adi Amrany
(74) *Attorney, Agent, or Firm* — Kilpatrick Townsend & Stockton LLP

(57) ABSTRACT

This disclosure describes a portable electronic device that includes a first housing component having an exterior-facing surface and an interior-facing surface; and a second housing component cooperating with the first housing component to define an interior volume. A seal fills an interface between the first and second housing components. Electrically conductive material that forms an electrically conductive pathway extends across portions of the interior and exterior-facing surfaces of the first housing component. The electrically conductive pathway is configured to transmit and/or receive signals or power between an exterior and interior of the portable electronic device.

14 Claims, 9 Drawing Sheets

Related U.S. Application Data continuation-in-part of application No. 16/122,787, filed on Sep. 5, 2018, now Pat. No. 10,491,041, and a continuation-in-part of application No. 16/122,766, filed on Sep. 5, 2018, now Pat. No. 10,381,881, and a continuation-in-part of application No. 16/122,799, filed on Sep. 5, 2018, now Pat. No. 10,855,110.

(60) Provisional application No. 62/725,202, filed on Aug. 30, 2018, provisional application No. 62/725,187, filed on Aug. 30, 2018, provisional application No. 62/554,945, filed on Sep. 6, 2017.

(51) Int. Cl.
*H05K 5/02* (2006.01)
*H05K 5/00* (2006.01)
*C23C 14/06* (2006.01)

(52) U.S. Cl.
CPC ......... *A61B 5/6898* (2013.01); *H05K 5/0086* (2013.01); *H05K 5/0095* (2013.01); *H05K 5/0217* (2013.01); *A61B 2560/0406* (2013.01); *A61B 2560/0431* (2013.01); *A61B 2560/0462* (2013.01); *A61B 2562/0238* (2013.01); *A61B 2562/182* (2013.01); *C23C 14/0641* (2013.01)

(56) References Cited

U.S. PATENT DOCUMENTS

| | | | |
|---|---|---|---|
| 4,063,111 A * | 12/1977 | Dobler | G04C 17/00 |
| | | | 307/116 |
| 4,322,833 A * | 3/1982 | Husted | G04G 21/08 |
| | | | 368/69 |
| 5,814,900 A | 9/1998 | Esser et al. | |
| 6,300,920 B1 | 10/2001 | Pertl et al. | |
| 6,348,070 B1 | 2/2002 | Teissl et al. | |
| 8,897,859 B2 | 11/2014 | Shimuta et al. | |
| 10,599,101 B2 | 3/2020 | Rothkopf et al. | |
| 10,729,347 B1 * | 8/2020 | Schleicher | A61B 5/6802 |
| 10,772,512 B2 * | 9/2020 | Klaassen | A61B 5/681 |
| 10,855,110 B2 | 12/2020 | Wittenberg et al. | |
| 2002/0055763 A1 | 5/2002 | Zarinetchi et al. | |
| 2003/0011527 A1 | 1/2003 | Kokorin et al. | |
| 2004/0051617 A1 | 3/2004 | Buswell | |
| 2007/0228833 A1 | 10/2007 | Stevens et al. | |
| 2008/0074112 A1 | 3/2008 | Abe et al. | |
| 2008/0079420 A1 | 4/2008 | Hrubes et al. | |
| 2008/0303479 A1 | 12/2008 | Park et al. | |
| 2009/0315680 A1 | 12/2009 | Arimura | |
| 2010/0033021 A1 | 2/2010 | Bennett | |
| 2010/0289341 A1 | 11/2010 | Ozaki et al. | |
| 2011/0115735 A1 | 5/2011 | Lev et al. | |
| 2011/0127951 A1 | 6/2011 | Walley et al. | |
| 2011/0164471 A1 | 7/2011 | Baarman et al. | |
| 2011/0200763 A1 * | 8/2011 | Tixhon | C03C 17/002 |
| | | | 427/569 |
| 2011/0304217 A1 | 12/2011 | Yamamoto et al. | |
| 2012/0032632 A1 | 2/2012 | Soar et al. | |
| 2012/0112552 A1 | 5/2012 | Baarman et al. | |
| 2012/0200169 A1 | 8/2012 | Urano | |
| 2012/0216847 A1 * | 8/2012 | Kumar | H02S 10/10 |
| | | | 136/201 |
| 2013/0049484 A1 | 2/2013 | Weissentern et al. | |
| 2013/0113422 A1 | 5/2013 | Lee et al. | |
| 2013/0314035 A1 | 11/2013 | Kohlschmidt et al. | |
| 2014/0024915 A1 * | 1/2014 | Jaakkola | A61B 5/6807 |
| | | | 600/388 |
| 2014/0143933 A1 | 5/2014 | Low et al. | |
| 2015/0015180 A1 | 1/2015 | Miller et al. | |
| 2015/0123604 A1 | 5/2015 | Lee et al. | |
| 2015/0195009 A1 | 7/2015 | Wang et al. | |
| 2015/0224883 A1 | 8/2015 | Ichikawa et al. | |
| 2015/0280444 A1 | 10/2015 | Smith et al. | |
| 2015/0326028 A1 | 11/2015 | Suzuki et al. | |
| 2015/0371768 A1 | 12/2015 | Graham et al. | |
| 2016/0058375 A1 * | 3/2016 | Rothkopf | A61B 5/0205 |
| | | | 600/301 |
| 2016/0111887 A1 | 4/2016 | Jeong | |
| 2017/0047635 A1 | 2/2017 | Wolentarski et al. | |
| 2017/0049352 A1 * | 2/2017 | Mirov | A61B 5/0533 |
| 2017/0077589 A1 | 3/2017 | Finn et al. | |
| 2017/0133880 A1 | 5/2017 | Wakisaka | |
| 2017/0214422 A1 | 7/2017 | Na et al. | |
| 2017/0224218 A1 * | 8/2017 | Tanaka | A61B 5/0048 |
| 2017/0293267 A1 | 10/2017 | Zhang | |
| 2017/0365766 A1 | 12/2017 | Boukai et al. | |
| 2018/0062430 A1 | 3/2018 | Matsumoto et al. | |
| 2018/0196396 A1 | 7/2018 | Cho et al. | |
| 2018/0248406 A1 | 8/2018 | Bae et al. | |
| 2018/0279517 A1 | 9/2018 | Jang et al. | |
| 2019/0072912 A1 * | 3/2019 | Pandya | G04G 21/08 |
| 2019/0125259 A1 * | 5/2019 | Huang | A61B 5/0205 |
| 2019/0204790 A1 | 7/2019 | Kim et al. | |
| 2019/0329653 A1 | 10/2019 | Ueta | |
| 2020/0064781 A1 | 2/2020 | Shim et al. | |

FOREIGN PATENT DOCUMENTS

| | | |
|---|---|---|
| JP | 2019060897 | 4/2019 |
| WO | 0059069 | 10/2000 |
| WO | 0180360 | 10/2001 |
| WO | 2009026253 | 2/2009 |
| WO | 2015199044 | 12/2015 |
| WO | 2016205508 | 12/2016 |

OTHER PUBLICATIONS

U.S. Appl. No. 16/122,799, First Action Interview Pilot Program Pre-Interview Communication, dated May 26, 2020, 14 pages.

U.S. Appl. No. 16/122,811, Non-Final Office Action, dated Jun. 12, 2020, 13 pages.

U.S. Appl. No. 16/122,766, "Notice of Allowance", dated Apr. 1, 2019, 11 pages.

U.S. Appl. No. 16/122,787, "First Action Interview Pilot Program Pre-Interview Communication", dated Feb. 21, 2019, 4 pages.

U.S. Appl. No. 16/122,811, Final Office Action, dated Mar. 9, 2021, 14 pages.

U.S. Appl. No. 16/122,811, "Non-Final Office Action", dated Nov. 17, 2020, 13 pages.

U.S. Appl. No. 16/526,668, "Notice of Allowance", dated Jan. 19, 2021, 14 pages.

European Patent Application No. 19167945.5, "Intention to Grant", dated Nov. 24, 2020, 9 pages.

* cited by examiner

FILM COATINGS AS ELECTRICALLY CONDUCTIVE PATHWAYS

CROSS REFERENCES TO RELATED APPLICATIONS

This application claims priority to U.S. Provisional Patent Application No. 62/725,187 and 62/725,202 both filed on Aug. 30, 2018, and is a continuation in part of U.S. patent application Ser. No. 16/122,766, filed Sep. 5, 2018, and is a continuation in part of U.S. patent application Ser. No. 16/122,787, filed Sep. 5, 2018, and is a continuation in part of U.S. patent application Ser. No. 16/122,799, filed Sep. 5, 2018, and is a continuation in part of U.S. patent application Ser. No. 16/122,811, filed Sep. 5, 2018, which claims priority to U.S. Provisional Patent Application No. 62/554,945, filed on Sep. 6, 2017. Each of these references is hereby incorporated by reference in their entirety and for all purposes.

FIELD

This application relates generally to the use of electrically conductive thin film coatings to route signals and sensor readings into and out of a device housing. In particular, the thin film coatings can extend through a sealed interface between housing components.

BACKGROUND

Portable electronic devices are increasingly taken to large varieties of locations and consequently periodically exposed to harsh environmental conditions. Operating in these harsh conditions can result in openings in a portable electronic device becoming ingress points that retain liquids or abrasive particles, leading to subsequent degradation in operation of the portable electronic device. Openings for input/output ports and various sensors can negatively impact a cosmetic appearance of the portable electronic device. For these reasons, alternatives to input/output ports and sensor openings are desirable.

SUMMARY

This disclosure describes various embodiments that relate to one or more layers of thin film being utilized to create an electrically conductive pathway extending out of a water resistance portable electronic device.

A portable electronic device is disclosed and includes the following: a first housing component having an exterior-facing surface and an interior-facing surface; a second housing component cooperating with the first housing component to define an interior volume; a seal filling an interface between the first and second housing components; and an electrically conductive pathway extending through the interface and arranged across portions of both the interior and exterior-facing surfaces of the first housing component.

A portable electronic device is disclosed and includes the following: a sensor window having an exterior-facing surface and an interior-facing surface; a sensor assembly configured to transmit and receive light through a portion of the sensor window; a housing component cooperating with the sensor window to define an interior volume; and electrically conductive material covering portions of both the interior-facing and exterior-facing surfaces of the sensor window and being electrically coupled to the sensor assembly.

A portable electronic device is disclosed and includes the following: a first housing component having a first surface and a second surface opposite the first side; a second housing component coupled to the first housing component; and an electrically conductive film extending from the first surface to the second surface.

Other aspects and advantages of the invention will become apparent from the following detailed description taken in conjunction with the accompanying drawings which illustrate, by way of example, the principles of the described embodiments.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1A:
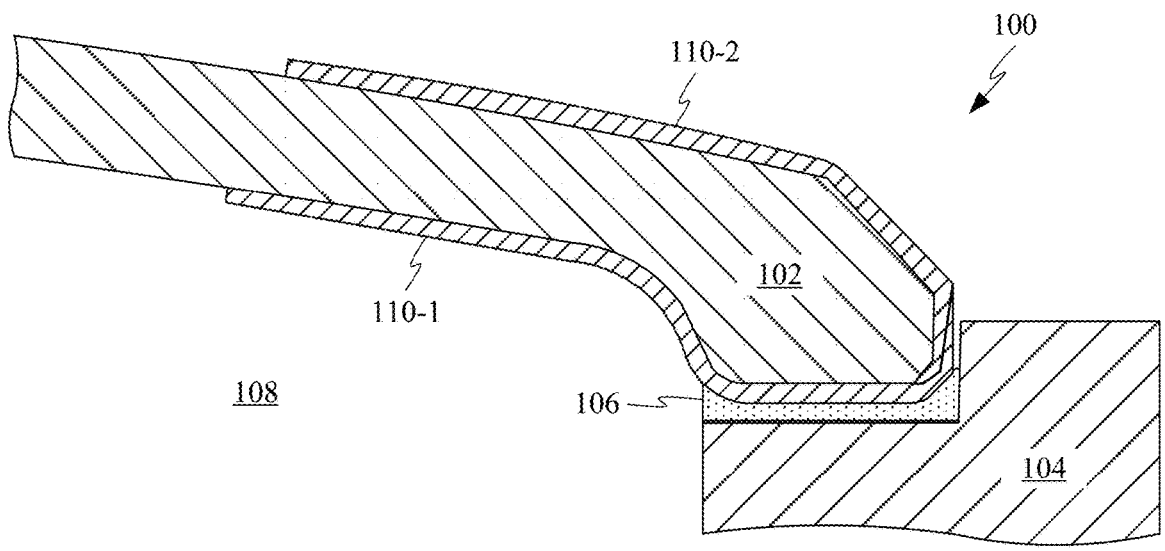
FIGS. 1A-1B show a device housing that includes a first housing component sealed to a second housing component by a seal element.

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

A portable electronic device can be made more robust by reducing and/or eliminating the number of openings leading from an interior of a device housing to an exterior of the device housing. Unfortunately, the incorporation of sensors and input/output sensors often require one or more openings that can negatively affect the robustness of the device. For example, an input/output port often includes a cavity for receiving an electrical plug. This cavity allows liquids to enter at least a portion of the device housing. While the cavity itself can be sealed against normal water intrusion, corrosive liquid or debris could be retained in the cavity and over time cause damage or degrade operation of the portable electronic device.

One solution to this problem is to position a layer of electrically conductive material on a housing component that extends through a sealing or water proofing element of the device housing. For example, a layer of electrically conductive material can be deposited upon and extend between peripheral regions of opposing surfaces of a first housing component. When the first housing component is sealed to a second housing component the deposited conductive material can provide a robust electrically conductive pathway leading into and out of the housing without impacting the water-resistance of the device housing. The electrically conductive pathway can be configured to relay sensor readings and/or power between the inside and outside of the device housing. In some embodiments, it can be beneficial to deposit the electrically conductive material upon a housing component formed from material that is unlikely to bend or deform. For example, a housing component formed from a glass, sapphire or ceramic substrate could be more likely to hold its shape than an aluminum substrate. Glass, sapphire and ceramic substrates also have the advantage of being electrically insulating, thereby allowing the electrically conductive pathways to be deposited directly on glass and ceramic substrates. By depositing the electrically conductive material on a substrate unlikely to undergo deformation, a likelihood of degradation of the electrically conductive pathway due to a drop or inadvertent collision is reduced. It is also desirable to use a robust electrically conductive material that is at least resistant to scraping off during normal use of the device. In some embodiments, the electrically conductive material can be deposited as a thin film having a thickness of between about 0.5 and 10 microns. A thickness of the thin film can be adjusted based on how much current is being conducted along the thin film. A thickness of the layer of film can also be increased in order to make electrically conductive pathways formed by the film more robust to various types of use.

In some embodiments, the aforementioned electrically conductive material can be positioned on an electrically conductive housing. For example, an aluminum housing component can be anodized to form a layer of aluminum oxide along an exterior surface of the housing component prior to depositing the electrically conductive material. In this way, the electrically conductive material can carry a signal or power without interference from the aluminum alloy disposed beneath the aluminum oxide layer.

These and other embodiments are discussed below with reference to FIGS. 1A-6; however, those skilled in the art will readily appreciate that the detailed description given herein with respect to these figures is for explanatory purposes only and should not be construed as limiting.

Figure 1B:
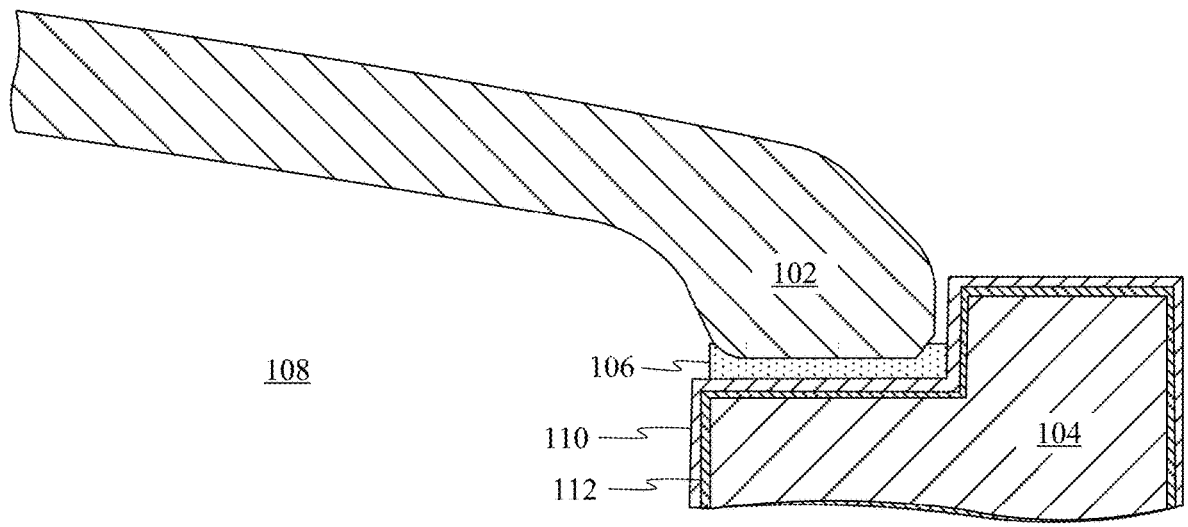

FIGS. 1A-1B show a device housing 100 that includes a first housing component 102 sealed to a second housing component 104 by a seal element 106. Seal element 106 is positioned within a gap between housing components 102 and 104 to prevent liquids, dust or debris from passing through the gap between first and second housing components 102 and 104. In this way, sensitive electrical components disposed within an interior volume 108 defined by housing components 102 and 104 can be protected from damage that could otherwise result from the intrusion of liquids, dust or debris. In particular, FIG. 1A shows how electrically conductive material 110 can be positioned upon opposing surfaces of a peripheral edge of first housing component 102. In this way, electrical signals and/or power can travel from interior volume 108 of device housing 100 to an exterior of device housing 100. The electrically conductive material can take many forms. In some embodiments, the electrically conductive material can be applied to first housing component 102 using a physical vapor deposition process. In some embodiments, the electrically conductive material can be plated onto a surface of first housing component 102. Generally, masking can be used to set a shape of the electrically conductive material upon surfaces of first housing component 102.

FIG. 1B shows an embodiment in which conductive material is arranged across surfaces of second housing component 104. When second housing component 104 is not formed from electrically insulating material, barrier layer 112 can be first positioned upon an exterior of second housing component 104 to avoid undesired interaction between electrically conductive material and second housing component 104. In some embodiments, barrier layer 112 can take the form of an electrically insulating layer formed by an anodization process. For example, a layer of aluminum oxide formed upon an exterior surface of an aluminum housing component.

Figure 2:
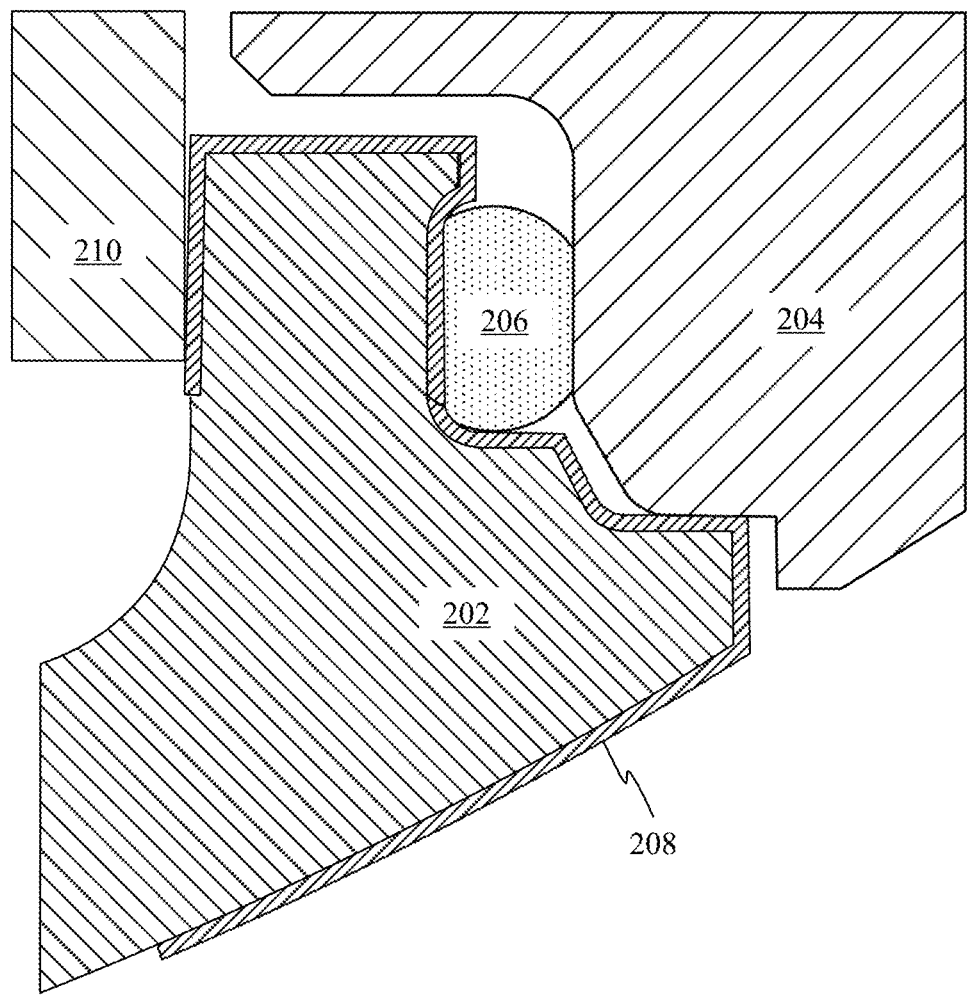
FIG. 2 shows an alternate configuration in which a gap between a first housing component and a second housing component is sealed by an O-ring.

FIG. 2 shows an alternate configuration in which a gap between a first housing component 202 and a second housing component 204 is sealed by an O-ring 206. In such a configuration, electrically conductive material 208 is still able to form an electrically conductive pathway leading from an interior to an exterior region of an associated electronic device. For example, electrical assembly 210, which is electrically coupled to an interior portion of electrically conductive material is able to measure inputs made at an exterior portion of electrically conductive material 208. For example, a connector or power source could engage the exterior portion of electrically conductive material 208 and power or signals could be received at electrical assembly 210. In some embodiments, electrically conductive material 208 could be arranged as a sensor. For example, two or more discrete pathways could be formed by electrically conductive material 208 and electrically coupled to electrical assembly 210. In such an embodiment, electrical assembly 210 could take the form of a sensor assembly configured to measure a voltage difference between the two or more discrete pathways. The difference in voltage can be used to measure the electrical conductance of a user's skin. Such a sensor can be referred to as a Galvanic Skin Response (GSR) sensor. In some embodiments, this measurement could be used in combination with other sensors such as an optical heart rate sensor to improve measurement of a user's heart rate. In some embodiments, the sensor assembly can instead take the form of an electrocardiogram sensor (ECG) capable of assessing electrical and muscular function of the heart.

Figure 3:
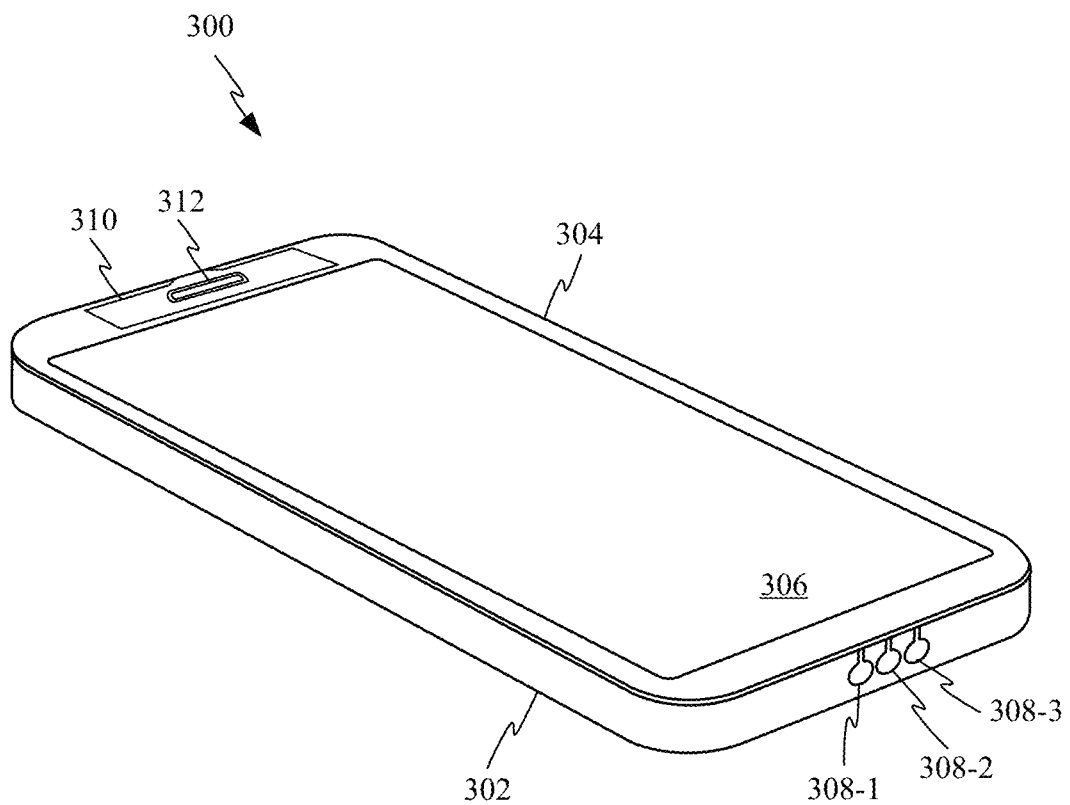
FIG. 3 shows a perspective view of an exemplary portable electronic device.

FIG. 3 shows a perspective view of an exemplary portable electronic device 300. Portable electronic device 300 includes a device housing 302 and display assembly 304 that cooperatively define an interior volume configured to accommodate various circuit boards, batteries and sensors. While not depicted in FIG. 3, device housing 302 and display assembly 304 can be joined together by a seal to form a water-resistant sealed housing that defines a cavity in which electrical components such as a processor, a computer-readable memory, one or more sensors, a battery, and the like, are housed. Display assembly 304 includes an active display area 306 across which a display shows a digital user interface. Display assembly 304 can also include a protective layer formed from glass, sapphire or ceramic material that allows the passage of light generated by the display of display assembly 304. The display can take the form of an LCD display, an OLED display, a micro LED display or other display type suitable for use with a portable electronic device. Electrically conductive material 308 can form multiple discrete regions on an exterior surface of device housing 302. Electrically conductive material 308 can extend through a gap between device housing 302 and the protective layer of display assembly 304. In some embodiments, electrically conductive material 308 can include multiple discrete contact regions 302-1, 302-2 and 302-3 that cooperatively act as a charging port for receiving energy to power an energy storage device along the lines of a battery within portable electronic device 300. For example, the discrete contact regions could form positive, negative and/or ground terminals. In this way, power can be received by portable electronic device 300 without the need for an opening that could reduce the water resistance of portable electronic device 300. In some embodiments, one or more magnets could be positioned within device housing 302 and proximate contact regions 302-1, 302-2 and 302-3 and be configured to align contacts of an electrical connector with contact regions 302-1, 302-2 and 302-3. In some embodiments, the electrically conductive material forming contact regions 302-1, 302-2 and 302-3 can be a highly electrically conductive material such as gold or copper suitable for accommodating substantial amounts of electrical current.

FIG. 3 also shows how in some embodiments, electrically conductive material 310 can be deposited upon a protective cover of display assembly 304 and be configured to sense contact between a user's ear and a portion of the protective cover defining an earpiece opening 312. Electrically conductive material 310 can extend through the gap between display assembly 304 and device housing 302, allowing circuitry supporting this ear sensor to be secured within electronic device 300. In some embodiments, electrically conductive material 310 can take the form of indium tin oxide, which is optically transparent. The optical transparency of indium tin oxide can allow a user to remain unaware of its presence and using an optically transparent electrically conductive material such as indium tin oxide would not adversely affect the cosmetic appearance of electronic device 300. It should be noted that portable electronic device could also include a second protective cover arranged across a back surface of device housing (not depicted) and that electrically conductive pathways could also extended through a gap or interface between the second protective cover and the device housing. In some embodiments, the gap can be filled by a seal element taking the form of a layer of adhesive that acts to both retain the second protective cover and the device housing together and prevent the intrusion of debris or liquid into the device.

Figure 4A:
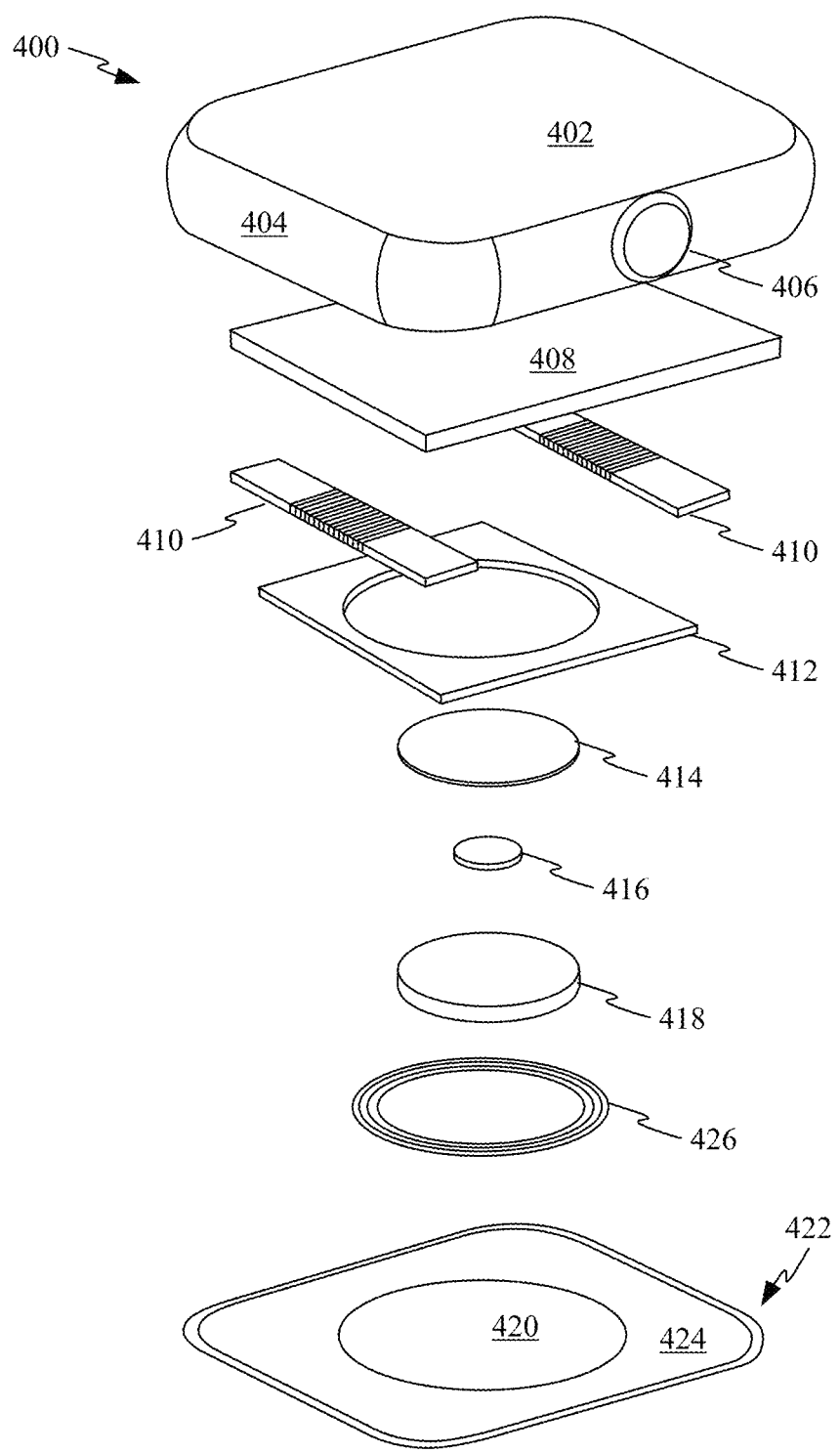
FIG. 4A shows an exploded view of a wearable electronic device.

FIG. 4A shows an exploded view of a wearable electronic device 400. Wearable electronic device 400 can include display 402 and upper housing component 404. In some embodiments, display 402 can be a touch sensitive display. Upper housing component 404 can be formed from a robust material such as metal, rigid plastic, or ceramics. Wearable electronic device 400 can include one or more user input controls such as crown 406 that allow a user to manipulate operation of wearable electronic device 400. Printed circuit board (PCB) 408 can include one or more processors configured to control operation of wearable electronic device 400. In some embodiments, PCB 408 can take the form of a system in chip that includes multiple processors packaged together on a printed circuit board. For example, a cellular communications processor, a near field communications processor and a main processing unit could all be positioned upon a single PCB. Wearable electronic device 400 can also include low frequency wireless charging coil assemblies 410 configured to interact with and receive power from a wireless charging mat. In some embodiments, low frequency wireless charging coil assemblies 410 can take the form of an electrically conductive coil wrapped around a ferritic substrate.

FIG. 4A also shows how wearable electronic device can include a wireless communications module 412. In some embodiments, wireless communications module 412 can include radios for communication over WiFi and/or cellular communication pathways. Wireless communications module 412 can include a central opening for accommodating other electrical components. DC shield 414 can have a circular geometry configured to fit within the central opening of wireless communications module 412. DC shield 414 can also be configured to prevent a magnetic field emitted by permanent magnet 416 from disrupting operation of components positioned upon PCB 408. Permanent magnet 416 can be configured to attract and retain a charging device to a surface of wearable electronic device 400. Sensor assembly 418 can include one or more optical sensors for optically measuring a user's heart rate. The optical sensors can include light emitters and light detectors, light from which extends through optically transparent sensor window 420 of lower housing component 422. Optically transparent sensor window 420 can be supported and surrounded by radio transparent member 424, which is configured to accommodate the passage of electromagnetic waves entering and exiting wearable electronic device 400. Wearable electronic device can also include a high frequency wireless charging coil 426 for receiving charging energy from a connector or charging device held in place by permanent magnet 416. In some embodiments, wireless charging coil 426 can take the form of a helical or flat coil in close proximity to optically transparent sensor window 420 and/or radio transparent member 424.

Figure 4B:
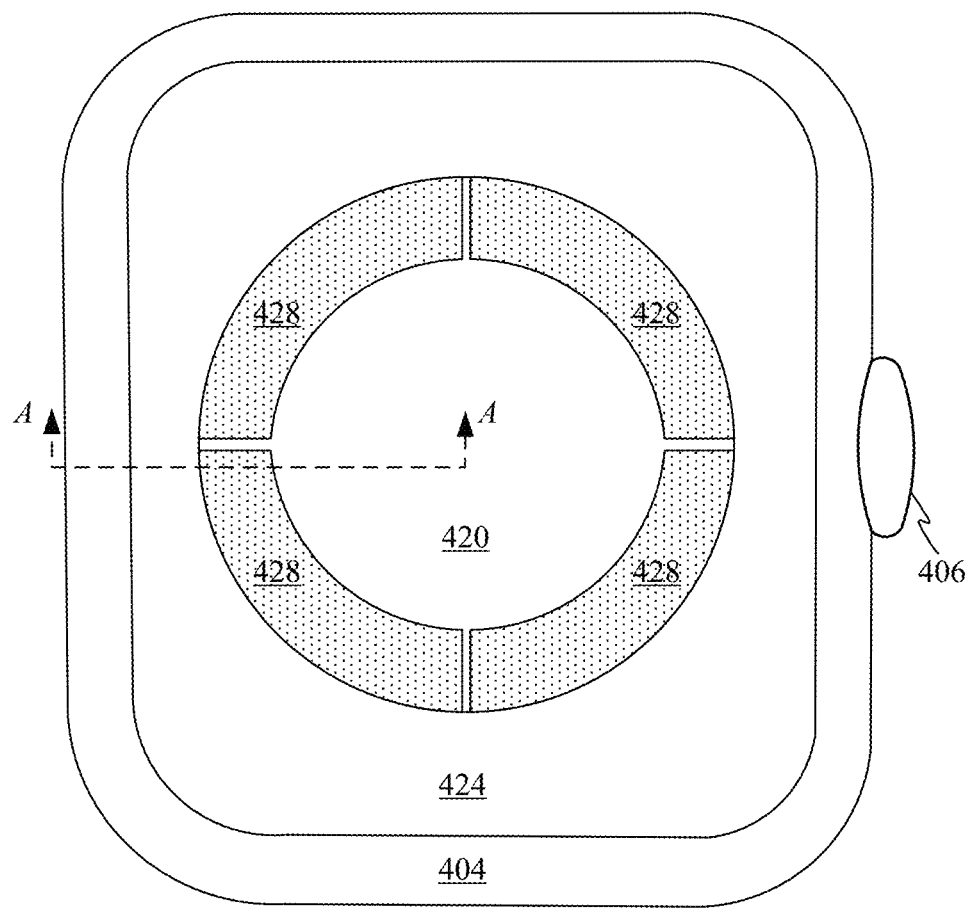
FIG. 4B shows a bottom view of the wearable electronic device depicted in FIG. 4A.

FIG. 4B shows a bottom view of wearable electronic device 400. In particular, electrically conductive material 428 is shown extending across a peripheral region of optically transparent window 420. This leaves a central region of optically transparent sensor window 420 unobscured and able to accommodate the passage of light associated with a sensor such as an optical heart rate sensor or photoplethysmography sensor (PPG). Electrically conductive material 428 is separated into four discrete regions but it should be appreciated that a larger or smaller number of regions could also be implemented. For example, in some embodiments, only two separate regions of electrically conductive material 428 can be positioned upon sensor window 420. When used as part of a sensor configuration, the two discrete regions allow for measurement of a voltage change between the two regions when the two regions are in direct contact with a user's skin. Four or more discrete regions would allow for redundancy and readings could be averaged together to improve accuracy. In embodiments where electrically conductive material 428 is used as a sensor, electrically conductive material 428 can take the form of a thin layer of chromium silicone carbon nitride applied by a PVD process. Chromium silicon carbon nitride alloys tend to have a high resistance to abrasion and low electrical conductivity. A low electrical conductivity reduces the amount of interference generated by placing the electrically conductive material in close proximity to other wireless components. Alternatively, electrically conductive material 428 can also take the form of titanium aluminum nitride, which also has robust mechanical properties and relatively low electrical conductivity. In particular, some titanium aluminum nitride alloys can have an electrical resistivity of about $2.8 \times 10^{-5}$ $\Omega$m, which is about three orders of magnitude higher than an electrical resistance of a highly conductive material such as Copper, which has an electrical resistance of about $1.68 \times 10^{-8}$ $\Omega$m. It should be noted that in addition to a PVD process other deposition processes can be used to deposit the electrically conductive material including by cathodic arc deposition and magnetron sputtering.

Figure 4C:
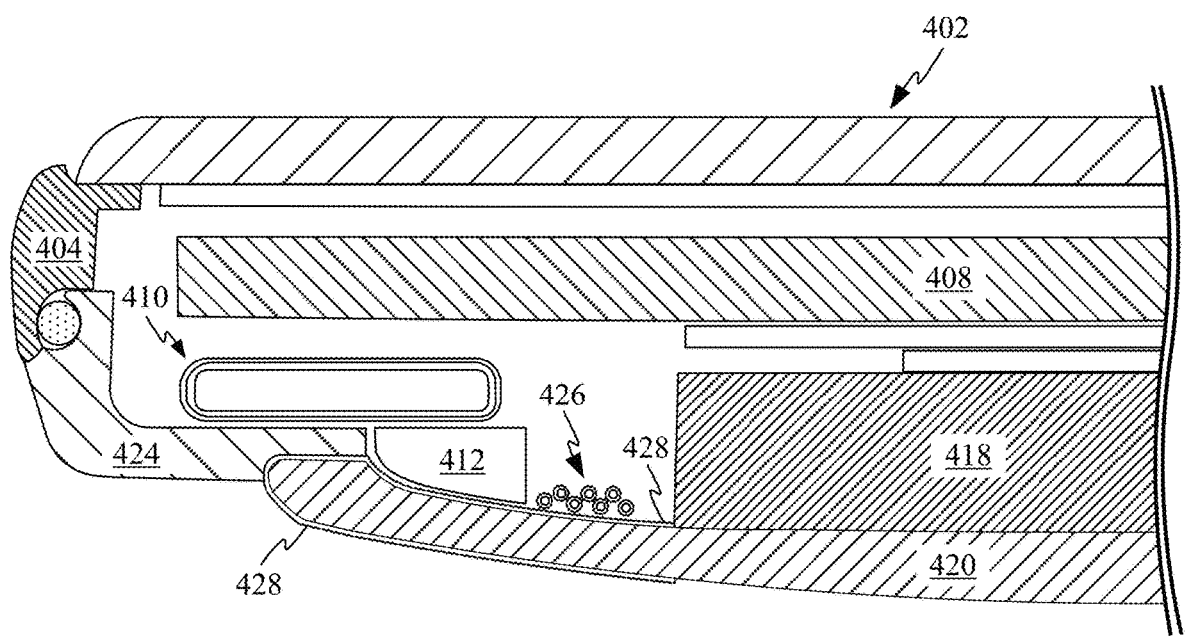
FIG. 4C shows a cross-sectional view of the wearable electronic device in accordance with section line A-A of FIG. 4B.

FIG. 4C shows a cross-sectional view of wearable electronic device 400 in accordance with section line A-A of FIG. 4B. In particular, electrically conductive material 428 is shown wrapping around a peripheral edge of sensor window 420 and connecting with sensor assembly 418. In this way, a voltage drop resulting from a user contacting two or more discrete regions of electrically conductive material 428 can be monitored and relayed to a processor associated with PCB 408 in order to measure one or more biometric parameters of a user of wearable electronic device 400. In some embodiments, sensor readings generated by sensor assembly 418 indicative of light received through sensor window 420 can be combined with the readings from the voltage drop across various regions of electrically conductive material 428 in order to provide a more complete biometric measurement of a user's physical state. It should also be noted that electrically conductive material 428 is positioned directly beneath three different wireless components including low frequency wireless charging coil assembly 410, wireless communications module 412 and high frequency wireless charging coil 426. While positioning electrically conductive material between a radio receiver or transmitter is generally considered counterintuitive, electrically conductive material can be deposited in a layer having a thickness of one or two microns. The thinness of the layer coupled with a relatively low electrical conductivity accommodates the flow of signals without unduly disrupting the free flow of wireless signals through the layer of electrically conductive material 428.

Figure 5A:
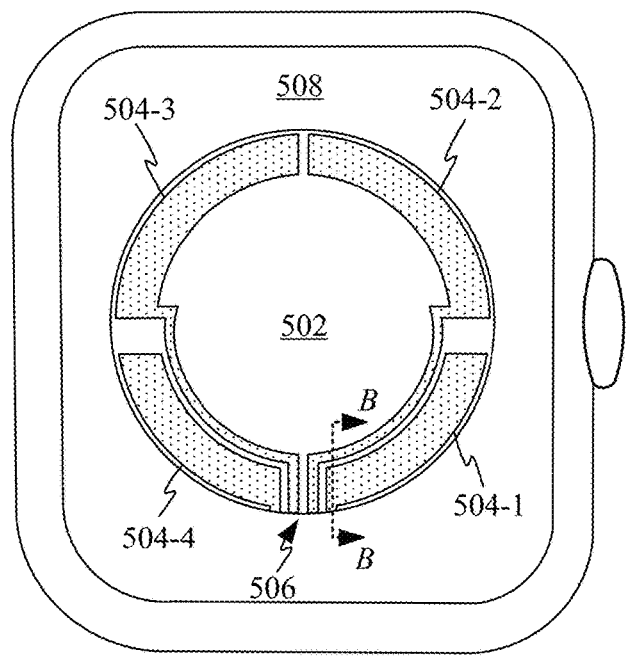
FIG. 5A shows a bottom view of a wearable electronic device similar to the wearable electronic device depicted in FIGS. 4A-4C.

FIG. 5A shows a bottom view of a wearable electronic device 500 similar to wearable electronic device 400. In particular, an optically transparent window 502 includes four discrete electrically conductive regions 504 formed from electrically conductive material and extending along a peripheral region of optically transparent window 502. In this embodiment, electrically conductive regions 504 extend through a narrow region 506 of an interface or contact area between optically transparent window 502 and radio transparent member 508.

Figure 5B:
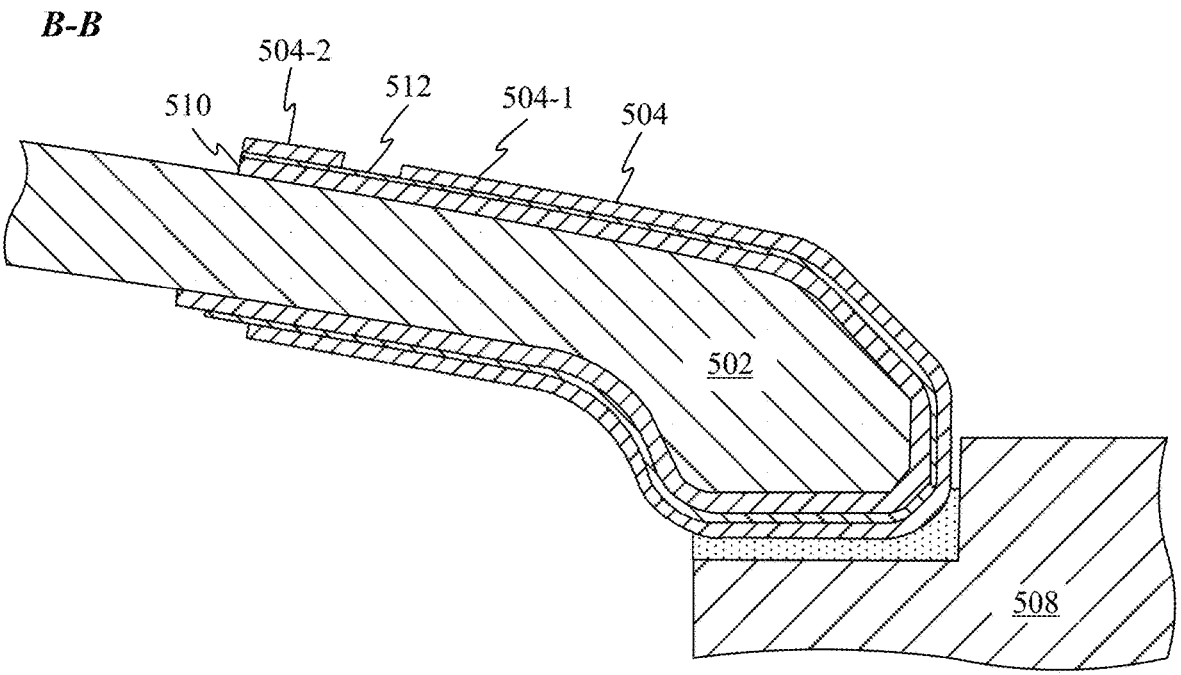
FIG. 5B shows a cross-sectional view of a portion of the wearable electronic device in accordance with section line B-B.

FIG. 5B shows a cross-sectional view of a portion of wearable electronic device 500 in accordance with section line B-B. In particular, FIG. 5B shows how electrically conductive regions 504 can be part of a multi-layer structure in which a first layer 510 of electrically conductive material is applied to optically transparent window 502. A second layer 512 of electrically insulating material can be added atop first layer 510. Second layer 512 can be formed of optically transparent material so as not to obscure a color or consistency of first layer 510. For example, second layer 512 can be formed from an optically clear epoxy or polymer material. A third layer 504 of electrically conductive material can be deposited atop second layer 512 to form discrete electrically conductive regions 504. Discrete electrically conductive regions 504 can be formed by masking portions of second layer 512 to form discrete electrically conductive pathways 504. Alternatively, portions of third layer 504 could be etched away to form the discrete electrically conductive pathways 504. When first layer 510 is formed from the same electrically conductive material as third layer 504, first layer 510 can at least partially obscure the patterning of third layer 504 allowing for a complex conductive region configuration with a cosmetically pleasing appearance. In some embodiments, a housing component could be entirely coated in the first layer allowing the pattern forming discrete electrically conductive pathways 504 to extend anywhere across the housing component and remain largely invisible to a user of wearable electronic device 500 instead of standing out as they do in FIG. 5A.

Figure 5C:
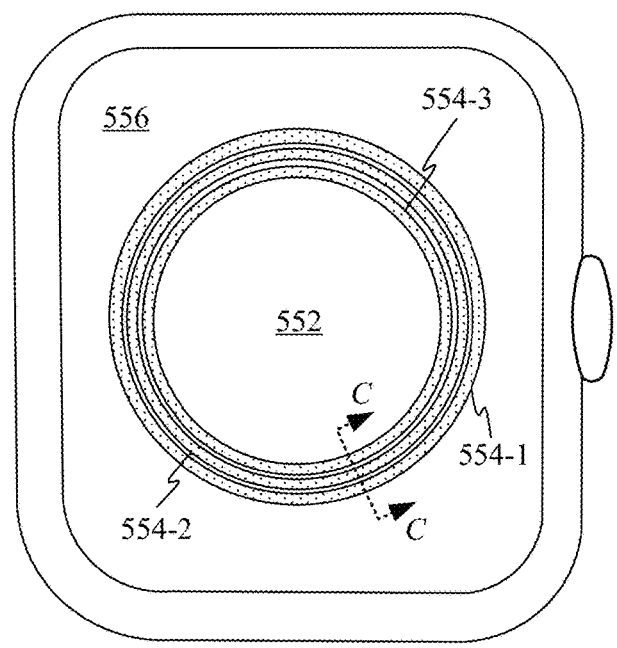
FIG. 5C shows a bottom view of another wearable electronic device similar to the wearable electronic devices depicted in FIGS. 4A-5B.

FIG. 5C shows a bottom view of a wearable electronic device 550 similar to wearable electronic devices 400 and 500. In particular, an optically transparent window 552 includes multiple concentric electrically conductive layers 554 formed from electrically conductive material and extending around a peripheral region of optically transparent window 552. In this embodiment, electrically conductive regions 554 extend through a gap between optically transparent window 552 and radio transparent member 556.

Figure 5D:
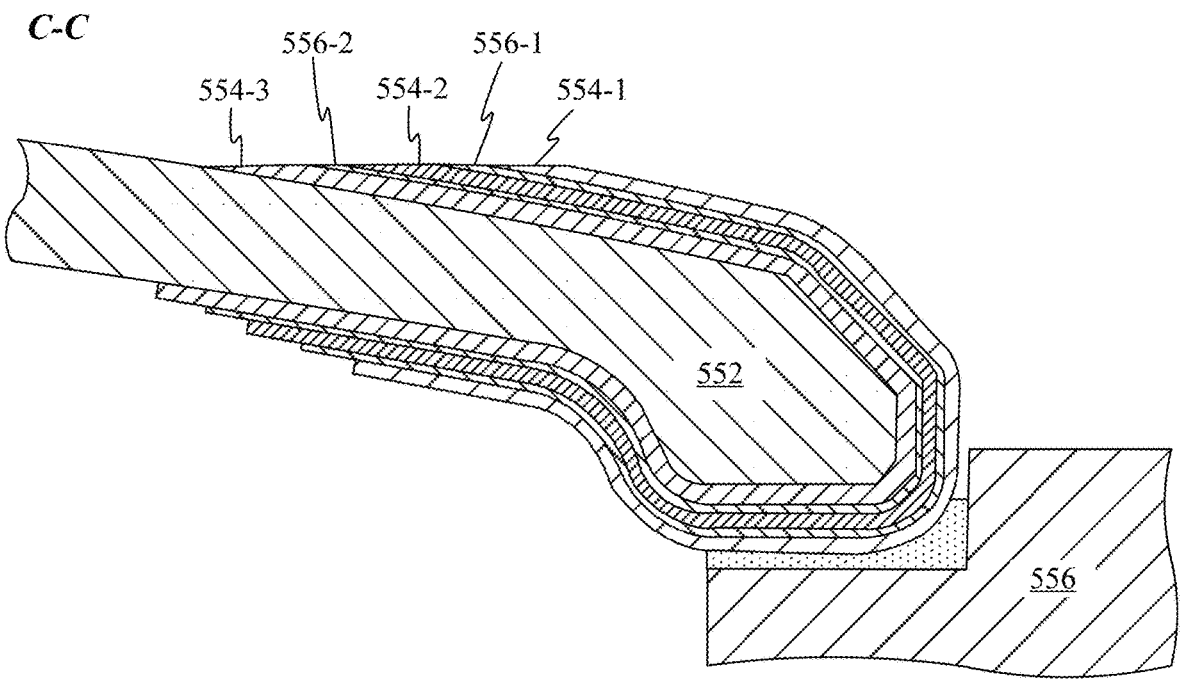
FIG. 5D shows a cross-sectional side view of a portion of the wearable electronic device depicted in FIG. 5C in accordance with section line C-C.

FIG. 5D shows a cross-sectional side view of a portion of the wearable electronic device 550 in accordance with section line C-C. In particular, electrically conductive layers 554-1, 554-2 and 554-3 are depicted as being stacked atop one another and separated by electrically insulating layers 556-1 and 556-2 so that all three electrically conductive layers can be exposed at an exterior surface of wearable electronic device 550. In some embodiments, electrically conductive layers 554-1 and 554-2 can be configured to receive power and electrically conductive layer 554-3 can be associated with the transference of data signals. In this way, a connector electrically coupled with electrically conductive layers 554-1, 554-2 and 554-3 can be configured to supply power and exchange data signals with one or more processors disposed within wearable electronic device 550. It should be noted that a thickness of the electrically conductive and electrically insulating layers are not shown to scale relative to a thickness of housing components 502 and 552. For example, housing components 502 and 552 may have a thickness of 1-10 mm while a thickness of the electrically conductive layers can be between 1-10 microns. It should also be appreciated that the multi-layer configurations depicted in FIGS. 5A-5B could also be applied to devices such as portable electronic device 300 depicted in FIG. 3.

Figure 6:
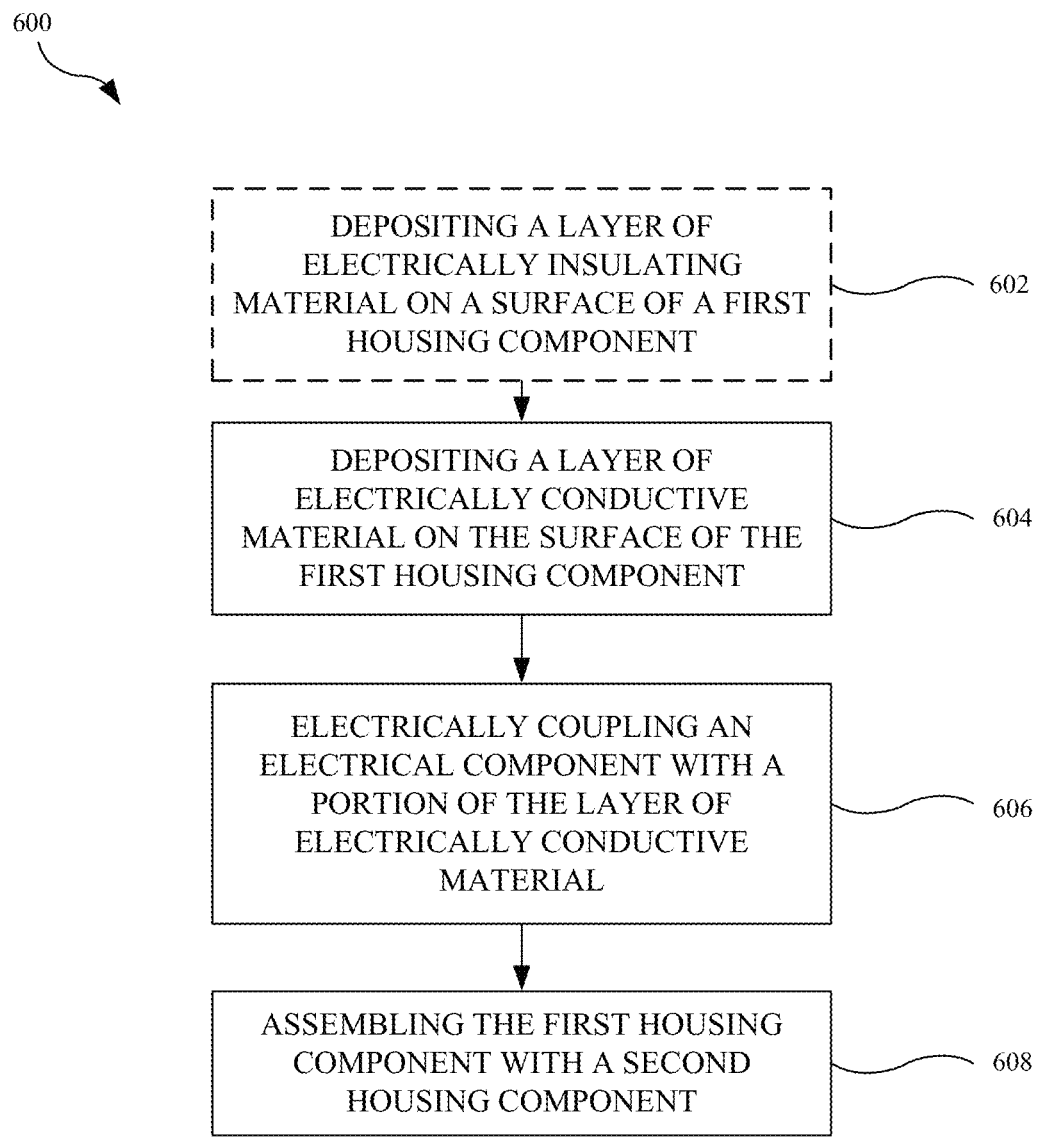
FIG. 6 shows a block diagram illustrating a method for creating an electrically conductive pathway extending from an interior to an exterior of an electronic device.

FIG. 6 shows a block diagram illustrating a method for creating an electrically conductive pathway extending from an interior to an exterior of an electronic device. At 602 a layer of electrically insulating material can be deposited upon a surface of a first housing component. This is an optional process and is particularly helpful when the housing component is formed from material having high electrical conductivity such as aluminum or stainless steel as the electrically insulating material can give the surface electrically insulating properties that prevent cross-talk between the housing component and conductive pathways or components affixed to the electrically insulating material. At 604, a layer of electrically conductive material is deposited upon the surface of the first housing component. The deposition process could be accomplished by a physical vapor deposition (PVD) process, a cathodic arc deposition process, a magnetron sputtering process or a plating process. Possible electrically conductive materials include gold, copper, titanium aluminum nitride or chromium silicon carbon nitride. In some embodiments, the deposition process can be a two-step process in which the electrically conductive material is deposited upon one side of the housing component at a time. While this might not be needed in a plating process, the two-step process could be implemented for PVD, cathodic arc or sputtering processes. In some embodiments, the electrically conductive material can form multiple contact regions. At 606, one or more electrical components of the electronic device can be coupled with a portion of the deposited layer of electrically conductive material. In some embodiments, the electrical component can be separately coupled to two or more different portions of the electrically conductive material. At 608, the first housing component is assembled with a second housing component in a manner such that the layer of electrically conductive material extends through an interface between the first and second housing components. A seal can also be positioned between the first and second housing components that is able to accommodate any variation in a geometry of the surface of the first housing component due to the deposited electrically conductive material. The seal element can be configured to inhibit the passage of liquids or debris between the first and second housing components.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling manufacturing operations or as computer readable code on a computer readable medium for controlling a manufacturing line. The computer readable medium is any data storage device that can store data, which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A portable electronic device, comprising:
    a housing having a lip defining an opening;
    an optically transparent sensor window covering the opening of the housing and cooperating with the housing to define an interior volume, the sensor window having an exterior-facing surface, an interior-facing surface, a central region, a peripheral region surrounding the central region, and a peripheral edge positionable adjacent to the lip of the housing;
    a seal filling a gap between the lip of the housing and the peripheral edge of the optically transparent sensor window;
    a multilayer electrically conductive film structure extending from a portion of the interior-facing surface of the optically transparent sensor window, between the lip and the optically transparent sensor window, to a portion of the exterior-facing surface of the optically transparent sensor window, the multilayer electrically conductive film structure comprising a first conductive film layer, an insulating layer overlying at least a first portion of the first conductive film layer, and a second conductive film layer overlying at least a first portion of the insulating layer, the multilayer electrically conductive film structure being positioned on the peripheral region of the optically transparent sensor window and wherein, when the portable electronic device is worn by a user, a second portion of the first conductive film layer and at least a portion of the second conductive film layer are positioned against a user's skin and are configured to measure respective first and second voltages of the user's skin; and
    a processor positioned in the interior volume and electrically coupled with the first and second conductive film layers, the processor configured to measure one or more biometric parameters of the user based on the first and second voltages.

2. The portable electronic device as recited in claim 1, further comprising an optical sensor assembly configured to transmit and receive light through the optically transparent sensor window.

3. The portable electronic device as recited in claim 1, wherein one or both of the first conductive film layer and the second conductive film layer is formed from material selected from the group consisting of chromium silicone carbon nitride and titanium aluminum nitride.

4. The portable electronic device as recited in claim 1, wherein the housing is a device housing component.

5. The portable electronic device as recited in claim 1, wherein the first and second conductive film layers have a thickness of between 0.5 and 10 microns.

6. The portable electronic device as recited in claim 1, wherein the first and second conductive film layers are deposited upon the optically transparent sensor window by one or more physical vapor deposition processes.

7. A portable electronic device, comprising:
    a housing having a lip defining an opening;
    a sensor window covering the opening of the housing and cooperating with the housing to define an interior volume, the sensor window having an exterior-facing surface, an interior-facing surface, a central region, a peripheral region surrounding the central region, and a peripheral edge positionable adjacent to the lip of the housing;
    a sensor assembly configured to transmit and receive light through the central region of the sensor window; and
    a multilayer electrically conductive film structure extending from a portion of the interior-facing surface of the sensor window, between the lip and the sensor window, to a portion of the exterior-facing surface of the sensor window, wherein the multilayer electrically conductive film structure comprises a first conductive film layer, an insulating layer overlying at least a first portion of the first conductive film layer, and a second conductive film layer overlying at least a first portion of the insulating layer, wherein the multilayer electrically conductive film structure is positioned on the peripheral region of the sensor window, wherein the first and second conductive film layers are electrically coupled to the sensor assembly, and wherein, when the portable electronic device is worn by a user, a second portion of the first conductive film layer and at least a portion of the second conductive film layer are positioned against a user's skin and are configured to measure respective first and second voltages of the user's skin; and a processor positioned within the interior volume and electrically coupled with the sensor assembly and the first and second conductive film layers, the processor configured to measure one or more biometric parameters of the user based on the first and second voltages and readings from the sensor assembly.

8. The portable electronic device as recited in claim 7, wherein the sensor assembly is configured to measure a heart rate of a user of the portable electronic device.

9. The portable electronic device as recited in claim 7, further comprising a seal filling a gap between the sensor window and the housing.

10. The portable electronic device as recited in claim 7, wherein the sensor assembly is configured to receive one or more signals from a portion respective portions of the first and second conductive film layers disposed on the exterior-facing surface of the sensor window.

11. A portable electronic device, comprising:

a first housing component having a lip defining an opening, the lip having a continuous and flat surface extending around a periphery of the opening;

a second housing component covering the opening of the first housing component and being coupled to the first housing component to define an interior volume, the second housing component having an interior surface, an exterior surface opposite the interior surface, a central region, a peripheral region surrounding the central region, and a peripheral edge positionable on the lip of the first housing component; and a multilayer electrically conductive film structure extending from a portion of the interior surface, between the lip of the first housing component and the second housing component, to a portion of the exterior surface, the multilayer electrically conductive film structure comprising a first conductive film layer, an insulating layer overlying at least a first portion of the first conductive film layer, and a second conductive film layer overlying at least a first portion of the insulating layer, the multilayer electrically conductive film structure being positioned on the peripheral region of the second housing component, wherein when the portable electronic device is worn by a user, a second portion of the first conductive film layer and at least a portion of the second conductive film layer are positioned against a user's skin.

12. The portable electronic device as recited in claim 11, wherein the first housing component is a device housing and the second housing component is a transparent article.

13. The portable electronic device as recited in claim 11, further comprising a seal disposed between the first and second housing components.

14. The portable electronic device as recited in claim 11, wherein the first and second conductive film layers are configured to contact a user's skin to measure respective first and second voltages of the user's skin while the user is wearing the portable electronic device, and wherein the portable electronic device further comprises a processor positioned in the interior volume and electrically coupled with the first and second conductive film layers, the processor being configured to measure one or more biometric parameters of the user based on the first and second voltages.

* * * * *

UNITED STATES PATENT AND TRADEMARK OFFICE
CERTIFICATE OF CORRECTION

PATENT NO. : 11,426,091 B2
APPLICATION NO. : 16/128210
DATED : August 30, 2022
INVENTOR(S) : Clavelle et al.

It is certified that error appears in the above-identified patent and that said Letters Patent is hereby corrected as shown below:

In the Claims

Column 10, Line 23: In Claim 1, replace "window" with --window,--

Signed and Sealed this
Eleventh Day of October, 2022

*Katherine Kelly Vidal*

Katherine Kelly Vidal
*Director of the United States Patent and Trademark Office*